United States Patent [19]

Stofko, Jr. et al.

[11] 4,361,637

[45] Nov. 30, 1982

[54] ELECTRON BIS-BENZOCARBAZOLE DONOR COMPOUNDS AND PHOTOCONDUCTIVE CHARGE TRANSPORT MATERIALS

[75] Inventors: John J. Stofko, Jr., St. Paul; Kenneth G. Kneipp, Maplewood; Terry J. Sonnonstine, White Bear Lake, all of Minn.

[73] Assignee: Minnesota Mining and Manufacturing Company, St. Paul, Minn.

[21] Appl. No.: 237,068

[22] Filed: Feb. 23, 1981

[51] Int. Cl.$^3$ .............................................. G03G 5/06
[52] U.S. Cl. ...................................... 430/58; 430/81; 430/900; 430/80

[58] Field of Search .................... 430/59, 81, 82, 900, 430/79, 80, 58

[56] References Cited

U.S. PATENT DOCUMENTS 4,025,341 5/1977 Rule .................................. 430/80 X

*Primary Examiner*—J. D. Welsh
*Attorney, Agent, or Firm*—Cruzan Alexander; Donald M. Sell; Mark A. Litman

[57] ABSTRACT

Organic electron donor compounds for use in electrophotographic constructions tend to suffer from problems of molecular weight non-uniformity and oxidation. Bis-benzocarbazole derivatives have been found to resist the oxidation and oligomerization which are a source of these problems.

14 Claims, No Drawings

ELECTRON BIS-BENZOCARBAZOLE DONOR COMPOUNDS AND PHOTOCONDUCTIVE CHARGE TRANSPORT MATERIALS

TECHNICAL FIELD

The present invention relates to novel compounds which are electron donor compounds and novel photoconductive charge transporting layers comprising these novel compounds in binders. These layers are particularly useful in imaging systems such as electrophotography or electroradiography.

BACKGROUND OF THE ART

The technology of electrophotography is commercially well established. A wide variety of processes and apparatus are used, although they have many characteristics in common. One of the more common forms of this technology involves the use of a plate having a photoconductive insulating layer, generally coated on a conductive layer. Imaging is effected by first uniformly electrostatically charging the surface of the photo-conductive layer and then exposing the charged layer to an image or pattern of activating electromagnetic radiation, usually visible or ultraviolet radiation. This exposure selectively enables the charge in the irradiated areas of the photoconductive insulator to dissipate. The charge which remains in the non-irradiated areas forms a latent image which may be further processed to form a more permanent record of the exposing image or pattern. The most common form of additional processing involves the attraction of particles of material selectively to the charged areas and fusing them to the photoconductive layer or transferring the particles in their imagewise distribution to another surface to which they are more permanently bound by an adhesive or by fusion of the particles themselves. A common electrophotographic construction comprises, in sequence, a substrate, a conductive layer, and a photoconductive insulating layer.

Typical classes of photoconductive materials useful in electrophotography include (1) inorganic crystalline photoconductors such as cadmium sulfide, cadmium sulfoselenide, cadmium selenide, zinc sulfide, zinc oxide, and mixtures thereof, (2) inorganic photoconductive glasses such as amorphous selenium, selenium alloys, and selenium-arsenic, and (3) organic photoconductors such as phthalocyanine pigments and polyvinyl carbazole, with or without binders and additives which extend their range of spectral sensitivity. These systems are well known in the art. For example, U.S. Pat. No. 3,877,935 discusses various problems associated with the crystalline and amorphous classes of photoconductors and shows the use of polynuclear quinone pigments in a binder as a photoconductive layer. U.S. Pat. No. 3,824,099 shows the use of squaric acid methine sensitizing dyes and triaryl pyrazoline charge transport materials as an electrophotographic construction. Cadmium sulfoselenide plates are shown in U.S. Pat. No. 3,764,315, and one of the original disclosures of the use of poly-N-vinylcarbazole as a photoconductive insulating layer is provided in U.S. Pat. No. 3,037,861. A number of diverse organic photoconductors have been disclosed since the development of the carbazole class of photoconductors such as quinones and anthrones (e.g., Hayashi et al., *Bull. Chem. Soc. Japan*, vol. 39, (1966) pp. 1670-1673), but the carbazoles have continued to attract the greatest attention.

Problems particularly associated with the use of carbazoles as a positive charge transporting material which is capable of supporting the injection of photoexcited holes from a photoconductive layer and is capable of transporting the injected holes also exist in this area of technology. The carbazole condensates with aldehydes as shown in U.S. Pat. No. 4,025,341 have a tendency to oligomerize. This oligomerization can cause a number of problems. The oligomers formed are not of a uniform molecular weight and carbazole content. This creates problems in purification and can create undesirable variations in photoconductive or charge transport properties. Triaryl methanes including a carbazole moiety (as shown in Xerox Disclosure Journal, Vol. 3, No. 1, Jan/Feb 1978, page 7) also tend to be sensitive to oxidation which converts them to an ionic species which will not act as a photoconductive insulator but rather will act as a conductor.

Japanese Pat. Publication No. 52-34735 discloses carbazole organic photoconductor materials which may have substituents thereon which would inherently prevent oligomerization of the carbazoles. This is not recognized in the disclosure and the carbazoles would still be subject to oxidation problems.

SUMMARY OF THE INVENTION

A novel class of electronically active organic donor compounds has the formula:

where X is

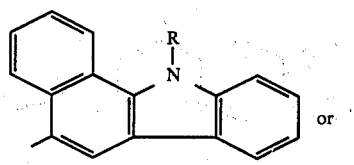 or

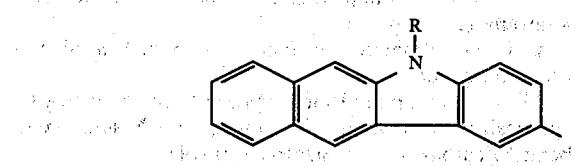

wherein R is an aliphatic, aromatic, or mixed aliphatic-aromatic group and Y is an aliphatic, aromatic, heterocyclic, or mixed aliphatic-aromatic group. For example, R and Y may be independently selected from alkyl groups, benzyl groups, phenyl groups, naphthyl groups, anthracyl groups, etc., with such various substituents as alkoxy groups, amine groups, alkyl groups, hydroxyl groups, and halogen atoms thereon.

These compounds have been found to be electron donor compounds and are useful in forming photoconductive electrically active insulating layers. They may be combined with polymeric binder materials to form photoconductive insulating layers and the compounds have a reduced sensitivity to oxygen and oligomerization.

DETAILED DESCRIPTION OF THE INVENTION

The novel compounds of the present invention are bis (benzocarbazoles) which may be represented by the formula

wherein X is

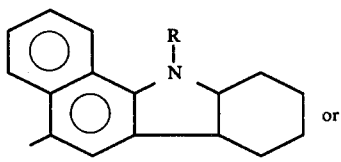

or

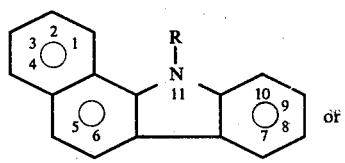

wherein R is an aliphatic, aromatic or mixed aliphatic-aromatic group and

Y is an aliphatic, aromatic or mixed aliphatic-aromatic group.

All of the compounds of the present invention may be synthesized by reacting the appropriate N-substituted benzo[a]carbazole or benzo[b]carbazole:

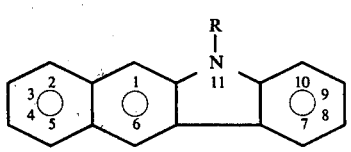

with the correspondingly appropriate aldehyde:

This process can be carried out in a solvent (e.g., ethanol) in the presence of an acid (e.g., HCl) catalyst. The reaction product may be isolated by simple filtration and washing. For example, in the reaction of 11-ethyl-benzo[a]carbazole with benzaldehyde in ethanol in the presence of HCl as a catalyst, because of the preferential reaction of the aldehyde at the 5-position of the 11-benzo[a]carbazole and the insolubility of the reaction product.

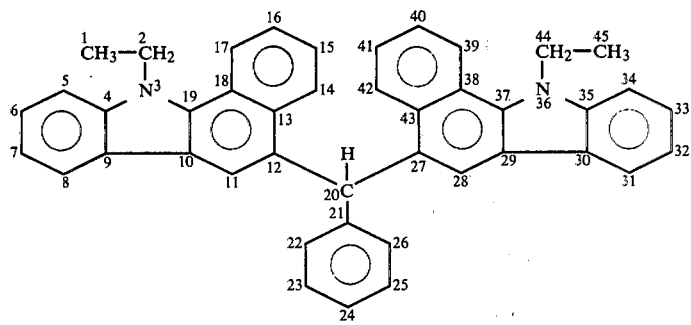

in ethanol, no oligomeric species are formed such as occur in a similar reaction with N-ethyl-carbazole. The reaction product is also stabilized against oxidation of the methine group by the rings ortho to the point at which the methine group is bonded to the benzocarbazole nucleus.

The benzocarbazole groups may bear substituents in positions other than N-substituents. Substituted benzocarbazole groups which are used as reagents in the synthesis of the bis(benzocarbazole)methanes of the present invention are well reported in the literature. The only significant limitation on the substitution of the reagents is that they not be substituted in the coupling position (position 5 for the benzo[a] and position 8 for the benzo[b]) of the benzocarbazoles. The substituents known in the art include alkyl, alkoxy, nitro, halogen, phenyl, naphthyl, benzyl, etc. The phenyl rings may be fused to the benzocarbazole by sharing two carbon atoms (e.g., 5,6 on benzo[a] and 9,10 on benzo[b]), three or four carbon atoms (e.g., 6,7 and bridging atoms on benzo[a] and benzo[b]). Heterocyclic rings and additional substituents on the substituted groups (e.g., -bromobutyl, -ethoxyethyl [i.e., a diethyl ether substituent], etc.) may be present. Preferably the substituents have fewer than 20 carbon atoms. The main effect of substitution is in the solubility characteristics of the compounds of the present invention. Substitution is most readily effected on position 8 of the benzo[a] carbazole and position 4 of the benzo[b] carbazole, but as noted above, substitution of the other positions is well known in the art. Substituted and non-substituted benzocarbazoles shall be distinguished, according to the practice of the present invention, by referring to formulae of compounds that may contain substitution as 'groups' and by referring to compounds which may not contain substitution as moieties.

R may, as previously stated, be selected from aliphatic, aromatic and mixed aliphatic-aromatic groups. These groups may or may not be substituted. If they are substituted, it would be preferred that they be electron donating substituents although electron withdrawing substituents may be tolerated. Preferably R is selected from alkyl groups of 1 to 20 carbon atoms, preferably n-alkyl groups of 2 to 20 carbon atoms, aryl groups such as phenyl or naphthyl groups, with phenyl groups preferred, alkaryl groups, for example benzyl groups, and allyl groups. Where the term 'group' is used anywhere in the practice of the present invention, as opposed to the term 'radical', the possibility of substitution is specifically intended to be included within the definition of that term. For example, n-alkyl radical may be only of the formula—$(CH_2)_n$—$CH_3$ while n-alkyl group may have hydrogen atoms on the n-alkyl radical substituted with other moieties such as halogen atoms, hydroxyl radicals, alkoxy radicals, alkyl radicals, amine radicals, cyano radicals, etc. Specific examples of useful R moieties are ethyl, n-butyl, n-propyl, 4-methoxybutyl, 3-chloropropyl, 8-hydroxyoctyl, phenyl, benzyl, allyl, p-ethylphenyl, m-tert-butylnaphthyl, p-diethylaminophenyl, stearyl, dodecyl, etc. R preferably has fewer than 20 carbon atoms, but may have up to 30 or more carbon atoms. The main influence of this group, except where electronic induction occurs because of a change of the nature of this group, is in the solubility of the compound.

Y may, as previously stated, be selected from aliphatic, aromatic, and mixed aliphatic-aromatic groups. These groups may or may not be substituted. Examples of useful moieties are methyl, ethyl, n-pentyl, nonyl, stearyl, tolyl, anisyl (m-, p-, and o-), p-chlorobenzyl, o-bromobenzyl, p-hydroxybenzyl, veratryl, isobutyl, terphthalyl, p-octyloxybenzyl, p-dimethylaminophenyl, t-butyl, etc. Preferred Y moieties are phenyl, tolyl, anisyl, and benzyl groups because of their availability. As with group R, the main influence of this group, except with regard to electron induction effects, is on the solubility of the compounds. Preferably Y has 20 or fewer carbon atoms, but up to 30 may be readily tolerated.

Various binder materials known in the art are useful with the electronically active donor compounds of the present invention. It is of course preferred that the binder be essentially optically transparent or at least transparent to the wavelengths of radiation to which the compounds (sensitized or not) are sensitive. Amongst the useful binders are poly(vinyl chloride), poly(siloxanes), poly(vinyl butyral), poly(vinyl acetate), styrene/acrylonitrile copolymers, polyacrylates, polymethacrylates, polycarbonates, polyepoxides, polyurethanes, polyamides, polyethers, polyesters, polyolefins as well as block, graft, random, and alternating polymers, copolymers, terpolymers and mixtures thereof and the like. The binders are preferably electrically inactive themselves. The preferred polymeric binders are polycarbonates, polyesters, and styrene/acrylonitrile copolymers. Coating aids, lubricants, surface active agents, and other adjuvants may be added to the composition.

For use of the materials of the present invention as electrophotographic layers, the organic electron donor compounds should be present as at least 20 percent by weight of the composition. Preferably the donor compound should be present as at least 25 or 35 percent by weight of the layer, and may comprise up to 100% by weight of the layer, excluding of course the sensitizer dye. The sensitizing dyes should be used in amounts which will increase the sensitivity of the composition. This is defined as an effective sensitizing amount of dye.

Ordinarily amounts of up to 10% by weight dye may be used, but certain constructions can be envisaged with as much as 90% by weight of dye and 10% by weight of organic electron donor compounds. Amounts of dye as small as 0.005 percent by weight can be useful. More preferred concentration ranges are between 0.05 and 5 percent by weight.

The photosensitive materials of the present invention may also be useful as photoconductive toners, photovoltaic devices, organic semiconductors, and the like, and may use concentrations of organic electronic donor compounds as low as 5 percent by weight.

Spectral sensitizers for photoconductive systems, as known in the art such as for example U.S. Pat. No. 3,037,861 are useful herein. These materials are generically classified as mineral acids, organic carboxylic acids, organic sulfonic acids, organic phosphonic acids, nitrophenols, acid anhydrides, metal halides, boron halides, gumones, aldehydes, and ketones. Copending U.S. patent application Ser. Nos. 237,067, 236,892, 236,653, and 236,654 filed the same day as this application disclose the sensitization of the benzocarbazoles of the present invention with (1) disulfone dyes, (2) quinoxaline dyes, (3) polyquinoid and polyanthraquinoid dyes, and (4) indolenine dyes respectively. The disclosure of those applications, with regard to the effect of those dyes in sensitizing the benzocarbazoles of the present invention are herein incorporated by reference in their entirety.

It has been surprisingly noted that the benzocarbazole-aldehyde condensation products of the present invention are better charge transport materials than the corresponding benzocarbazoles by themselves. This is surprising because it is the benzocarbazole nucleus which is the electronically active portion of both molecules. Even when benzocarbazoles were used in reasonably higher molecular proportions to the binder than were the condensates, the condensates would still perform better.

These and other aspects of the present invention will be shown in the following examples.

EXAMPLE 1

Synthesis of bis-5,5'-(N-ethylbenzo[a]carbazolyl)phenylmethane.

Into a round bottom flask equipped with a reflux condenser and a mechanical stirrer were added 22.4 grams (0.1 mole) of N-ethylbenzo[a]carbazole and 5.3 grams (0.05 mole) of benzaldehyde. Two hundred milliliters of ethanol acidified with 8 ml of concentrated hydrochloric acid were then added. The mixture was stirred at reflux under a nitrogen atmosphere for sixteen hours. The insoluble, pure white product was isolated by filtration, washed with 100 ml of ethanol, and dried in a vacuum oven. The yield was 95% of the theoretic calculation.

EXAMPLES 2-17

In a manner substantially identical to that of the previous example, electronically active electron donor compounds of the present invention were obtained by condensing N-ethylbenzo[a]carbazole with each of the following aldehydes in equimolar replacement for the benzaldehyde:
2. p-tolualdehyde
3. m-tolualdehyde
4. o-tolualdehyde 5. p-anisaldehyde
6. m-anisaldehyde
7. o-anisaldehyde
8. p-chlorobenzaldehyde
9. p-bromobenzaldehyde
10. o-bromobenzaldehyde
11. p-hydroxybenzaldehyde
12. α-naphthaldehyde
13. veratraldehyde
14. p-octyloxybenzaldehyde
15. iso-butyraldehyde
16. n-nonylaldehyde
17. terphthaldehyde

EXAMPLES 18–21

In a manner substantially identical to that of Example 1, the following combinations of carbazoles and aldehydes were used to synthesize compounds of the present invention.
18. benzo[a]carbazole and benzaldehyde
19. N-ethylbenzo[b]carbazole and benzaldehyde
20. N-ethyldibenzo[a,g]carbazole and benzaldehyde
21. N-ethyl-8-methoxybenzo[a]carbazole and benzaldehyde The addition of any of the compounds produced in Examples 1–21 to electrically inert polymeric binders formed positive charge transport layers. These layers could be coated on photoconductive charge generation layers and were capable of supporting injected photogenerated holes from the photoconductive layer and allowed the transport of these holes through the transport layer to selectively discharge the surface charge.

EXAMPLES 22–27

An electrophotographic plate was constructed of three layers. A photoconductive charge generation layer was coated onto a conductive glass substrate by conventional vapor deposition of a 0.5 micron thick amorphous selenium/tellurium alloy (95 atomic percent selenium and 5 atomic percent tellurium) using a resistive heater. The charge generation layer was then overcoated with solutions of electron donor compounds in organic polymers. In each of these examples the amounts of the electron donor compound and resin were varied to keep the molar ratio of the two constant with respect to the molar ratio of the 40/60 weight ratio of N-ethylbenzocarbazole to poly (4,4'-isopropylidenediphenylene carbonate) used in Example 1. This solution was provided as a 10% solids solution in 1,2-dichloroethane and coated out at 75 microns wet thickness to provide a dry charge transport layer 7 microns thick. The samples were air dried at room temperature for at least twelve hours before evaluation.

Each of the plates were negatively charged by a screened corona charging device and then exposed to a 90 foot candle tungsten illumination. The surface potential was monitored using an electrostatic voltmeter. The photodischarges at that level of exposure were essentially instantaneous to a residual potential voltage level. The performance of various devices, with the electron donor compounds noted, are shown in the following Table. The percent discharge was determined as the ratio of the initial potential ($V_i$) minus the residual potential ($V_r$) divided by the initial potential and multiplied by 100%. That is $$\frac{V_i - V_r}{V_i} \times 100\%.$$

TABLE

| Example | Compound | Initial Potential (volts) | Residual Potential (volts) | Discharge (%) |
|---|---|---|---|---|
| 22 | 19 | 605 | 32 | 95 |
| 23 | 6 | 608 | 74 | 88 |
| 24 | 5 | 670 | 110 | 84 |
| 25 | 1 | 618 | 118 | 81 |
| 26 | 12 | 593 | 126 | 79 |
| 27 | N—ethylbenzo[a]carbazole | 569 | 232 | 59 |

As an alternate means of evaluation, the field dependence of the initial discharge rates under low level illumination conditions at 500 nm were measured. Since the initial discharge rate is proportional to the photoinjection efficiency under emission limited conditions, a direct measure of the field dependence of the hole photoinjection efficiency can be obtained. Using electron donor compound 19 on Se(Te), the classic $E^{0.5}$ field dependence for photogeneration in amorphous Se was observed. This confirms that there is essentially no barrier to hole injection from amorphous Se(Te) when the materials of the present invention are used as charge transport layers.

An electrophotographic device produced according to this example exhibited improved xerographic performance and was capable of use in forming visible images by fixation of toner particles.

An electrophotographic device was prepared by first vacuum depositing about 1.0μ thick amorphous Se/Te (94 atomic percent Se/6 atomic percent Te, 25 ppm chlorine) onto a glow discharge cleaned, flexible, aluminized polyester web (100μ thick) using resistive heating techniques. The Se/Te charge generation layer was then overcoated with a ten percent solids solution [50% (wt) 1,2-dichloroethane/50% (wt) methylene dichloride] of [40% (wt) electron donor compound of examples 1–21/60% (wt) Vitel PE200 copolyester of terephthalic acid, isophthalic acid and ethylene glycol]. About 75μ wet coating thickness produced a dry transport layer coating thickness of 5–7μ.

An electrophotographic device produced according to this example exhibited improved xerographic performance and was preferred for use in forming visible images.

EXAMPLES 28–35

The effect of varying the substituent R on the donor compounds of the present invention were evaluated. The following materials were formed by condensation of the described materials.

| Compound | Carbazole | Aldehyde |
|---|---|---|
| A | N—allylbenzo[a]carbazole | benzaldehyde |
| B | N—benzylbenzo[a]carbazole | benzaldehyde |
| C | N—phenylbenzo[a]carbazole | benzaldehyde |
| D | N—propylbenzo[a]carbazole | benzaldehyde |
| E | N—ethylbenzo[a]carbazole | p-isopropylbenzaldehyde |

Electrophotographic devices were formed on a polyethyleneterephthalate substrate bearing an aluminum layer thereon. A one micron layer of Perylene Red (3,5-dimethylphenyl Perylene Red) was vapor deposited onto the aluminum layer and insulating photoconductive charge transport layers according to the present invention was coated on at about 5 mils (1.25×10⁻⁴ m) wet thickness and dried. The layers comprised sixty percent by weight of a polymer (VITEL® PE200 Polyester) and forty percent by weight of the charge transport donor compound:

28. Bis-benzocarbazolephenylmethane (Compound 1)
29. p-methoxy-bis-benzocarbazolephenyl-methane (Compound 21)
30. Compound E
31. 20% Bis-benzocarbazolephenylmethane (Compound 1) and 20% Compound D
32. Compound D
33. Compound A
34. Compound C
35. Compound B The sensitometric data from these elements are shown in the following Table. T represents the thickness of the coating in micrometers, Decay is the percent of dark decay, Speed is the amount of light in foot-candle-seconds necessary to reach $V_{o/2}$ and $T_r$ is the time constant for the voltage drop during exposure as expressed in the relationship $$V = V_r e^{-t/T_r}$$

wherein V is the voltage at any time, $V_r$ is the residual voltage, e is the natural logarithm base, and t is the length of time of the exposure.

| Ex. | $V_1$ | $V_o$ | T | Decay | Speed | $V_r$ | $T_r$ | Remarks |
|---|---|---|---|---|---|---|---|---|
| 28 | 338 | 325 | 5.7 | 3.8 | 0.828 | 33.6 | 4.95 | 1,4 |
| 29 | 386 | 368 | 6.4 | 4.7 | 0.565 | 25.9 | 1.89 | 1,5 |
| 30 | 604 | 572 | 8.6 | 5.3 | 5.11 | 117 | 5.28 | 3,5 |
| 31 | 652 | 636 | 14.2 | 2.5 | 1.24 | 110 | 6.86 | 3,7 |
| 32 | 572 | 556 | 8.5 | 2.8 | 1.49 | 117 | 15.9 | 2,6 |
| 33 | 428 | 412 | 7.0 | 3.7 | 0.911 | 49.5 | 7.20 | 1,7 |
| 34 | 920 | 902 | 8.5 | 2.0 | — | 755 | 7.50 | 2,7,8 |
| 35 | 620 | 600 | 9.3 | 3.2 | 1.87 | 197 | 23.0 | 2,7 |

Remarks

1. Coating solution 10% solids in 50/50 dichloroethane/methylene dichloride.
2. Coating solvent of 1, but with 16% solids.
3. Coating solvent of 1 and 2, but with 20% solids.
4. Coating solvent 50/50 dichloroethane/methylene dichloride.
5. Coating solvent 50/50 methylethylketone/toluene.
6. Coating solvent 2/1 methylethylketone/toluene.
7. Coating solvent dichloroethane.
8. Large residual potential obscured white light response.

EXAMPLE 36

In a further embodiment of an electrophotographic device, the charge generation layer was prepared by vacuum deposition of about 1.0μ thick arsenic triselenide ($As_2Se_3$) onto a glow discharge cleaned flexible, aluminized polyester web (100μ thick) using resistive heating techniques. The $As_2Se_3$ charge generation layer was then overcoated with a ten percent solids solution in [50% (wt) 1,2-dichloroethane/50% (wt) methylene dichloride] of [40% (wt) of the electron donor compound of Example 1/60% (wt) polyester]. About a 5 mil (125μ) wet coating thickness produced a dry transport layer with a coating thickness of 8–10μ.

The electrophotographic device produced according to this example exhibited improved xerographic performance and can be utilized in forming visible images.

We claim:

1. An electronically active photoconductive insulating layer comprising a polymeric binder and an electrically active donor compound of the formula

where X is a group selected from

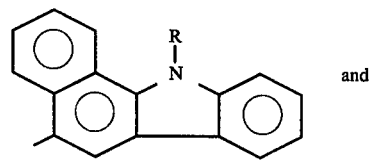

wherein R and Y are independently selected from the group consisting of aliphatic, aromatic, heterocyclic, and mixed aliphatic-aromatic groups.

2. The layer of claim 1 wherein Y is an aromatic group.

3. The layer of claims 1 or 2 wherein R is an alkyl group of 2 to 20 carbon atoms, phenyl group, naphthyl group or benzyl group.

4. The layer of claim 1 wherein Y is phenyl and R is n-alkyl of 2 to 20 carbon atoms.

5. The layer of claim 1 wherein X is a moiety selected from

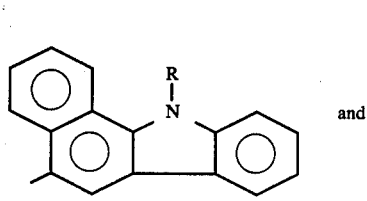

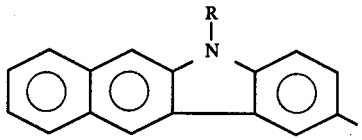

6. A photoconductive element comprising, in sequence, a conductive layer, a charge generating layer, and the photoconductive insulating layer of claims 1, 2, or 4.

7. A photoconductive element comprising a conductive layer and the layer of claims 1 or 2.

8. A photoconductive element comprising a conductive substrate and the layer of claim 2 wherein R is selected from the class consisting of an alkyl group of 2 to 20 carbon atoms, phenyl group, naphthyl group, or benzyl group.

9. An imaging process comprising providing an electrical charge on an element comprising in sequence a conductive layer, a photoconductive charge generating layer and the photoconductive insulating layer of claim 1, irradiating said charged element with a pattern of radiation to selectively cause areas of said charge to be conducted to said conductive layer, and selectively attracting material to either the charged or uncharged areas of said element to form an image.

10. The process of claim 9 wherein said image is transferred to another surface by contact therewith.

11. The layer of claims 1, 2 or 4 wherein X contains substituents on non-coupling positions other than the nitrogen atom, and such substituents are selected from the group consisting of alkyl, alkoxy, nitro, halogen, phenyl, naphthyl and benzyl.

12. The element of claim 6 wherein X contains substituents on non-coupling positions other than the nitrogen atom, and such substituents are selected from the group consisting of alkyl, alkoxy, nitro, halogen, phenyl, naphthyl and benzyl.

13. The element of claim 7 wherein X contains substituents on non-coupling positions other than the nitrogen atom, and such substituents are selected from the group consisting of alkyl, alkoxy, nitro, halogen, phenyl, naphthyl and benzyl.

14. The process of claims 9 or 10 wherein X contains substituents on non-coupling positions other than the nitrogen atom, and such substituents are selected from the group consisting of alkyl, alkoxy, nitro, halogen, phenyl, naphthyl and benzyl.

* * * * *